(12) United States Patent
Högdahl

(10) Patent No.: US 10,661,019 B2
(45) Date of Patent: May 26, 2020

(54) MEDICAMENT DELIVERY DEVICE

(71) Applicant: CAREBAY EUROPE LTD, Sliema (MT)

(72) Inventor: Stefan Högdahl, Stockholm (SE)

(73) Assignee: SHL MEDICAL AG, Zug (CH)

(*) Notice: Subject to any disclaimer, the term of this patent is extended or adjusted under 35 U.S.C. 154(b) by 143 days.

(21) Appl. No.: 15/776,308

(22) PCT Filed: Nov. 1, 2016

(86) PCT No.: PCT/EP2016/076295
§ 371 (c)(1),
(2) Date: May 15, 2018

(87) PCT Pub. No.: WO2017/089078
PCT Pub. Date: Jun. 1, 2017

(65) Prior Publication Data
US 2018/0326158 A1 Nov. 15, 2018

(30) Foreign Application Priority Data
Nov. 27, 2015 (SE) ..................... 1551550

(51) Int. Cl.
*A61M 5/315* (2006.01)
*A61M 5/31* (2006.01)
(Continued)

(52) U.S. Cl.
CPC ...... *A61M 5/31511* (2013.01); *A61M 5/2033* (2013.01); *A61M 5/24* (2013.01);
(Continued)

(58) Field of Classification Search
CPC .. A61M 5/2033; A61M 5/20; A61M 5/31551; A61M 5/3202; A61M 5/315;
(Continued)

(56) References Cited

U.S. PATENT DOCUMENTS 8,398,594 B2 * 3/2013 Streit ................. A61M 5/2033
604/135
2012/0123350 A1 5/2012 Giambattista et al.

FOREIGN PATENT DOCUMENTS

| CN | 102917743 A | 2/2013 |
| GB | 2424838 A | 10/2006 |

(Continued)

OTHER PUBLICATIONS

International Search Report and Written Opinion for PCT App. No. PCT/EP2016/076295, dated Jan. 24, 2017.

*Primary Examiner* — Nathan R Price
*Assistant Examiner* — Tania Ismail
(74) *Attorney, Agent, or Firm* — McDonnell Boehnen Hulbert & Berghoff LLP

(57) ABSTRACT

A medicament delivery device having a housing, arranged to accommodate a medicament container and a power unit, where the power unit has a plunger rod, a drive spring, operably arranged to act on the plunger rod and on said medicament container, an actuator having holding elements that can releasably hold the plunger rod with said drive spring in a tensioned state, and an actuator sleeve operably connected to said actuator for releasably locking said holding elements in a holding state. The medicament delivery device also can have a medicament delivery member guard slidably movable in said housing that can act on said actuator sleeve for setting said holding elements with said actuator sleeve in a first activation state; an activator unit arranged to be manually operated and which is operably connected to said plunger rod for setting said holding elements with said actuator sleeve in a second activation state.

18 Claims, 13 Drawing Sheets

(51) Int. Cl.
*A61M 5/24* (2006.01)
*A61M 5/20* (2006.01)

(52) U.S. Cl.
CPC ...... *A61M 5/3146* (2013.01); *A61M 5/31553* (2013.01); *A61M 5/31558* (2013.01); *A61M 5/31575* (2013.01); *A61M 5/31576* (2013.01); *A61M 5/31585* (2013.01); *A61M 5/31561* (2013.01); *A61M 5/31593* (2013.01); *A61M 2005/3104* (2013.01); *A61M 2005/3152* (2013.01); *A61M 2205/586* (2013.01)

(58) Field of Classification Search
CPC .......... A61M 5/31541; A61M 5/31571; A61M 5/31585; A61M 5/31515; A61M 5/31566; A61M 5/31511; A61M 5/3146; A61M 5/31576; A61M 5/31561; A61M 2005/2477
See application file for complete search history.

(56) References Cited

FOREIGN PATENT DOCUMENTS

| | | |
|---|---|---|
| TW | 201102120 A | 1/2011 |
| WO | 2006/062788 A2 | 6/2006 |
| WO | 2011/005177 A1 | 1/2011 |
| WO | 2011/121061 A1 | 10/2011 |
| WO | 2015/110529 | 7/2015 |

* cited by examiner

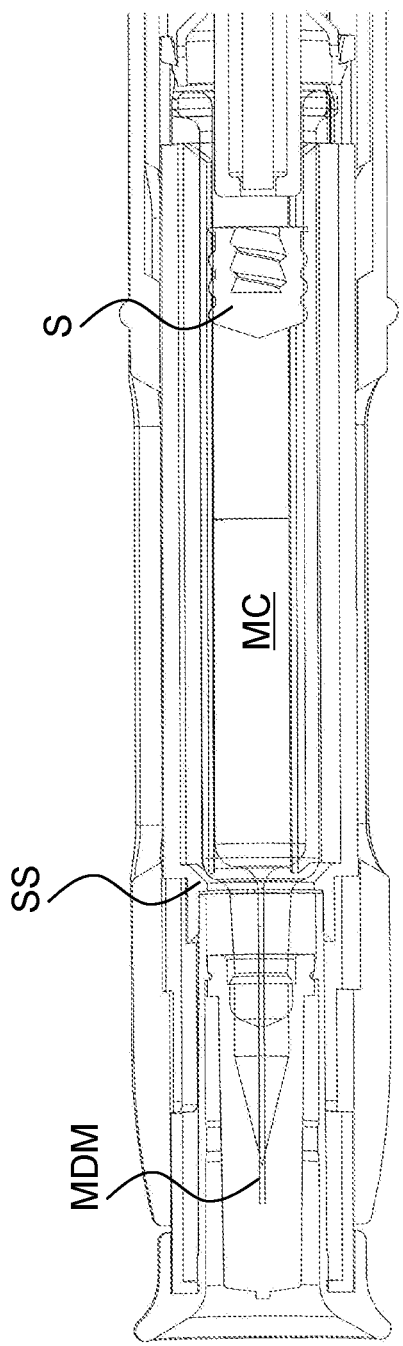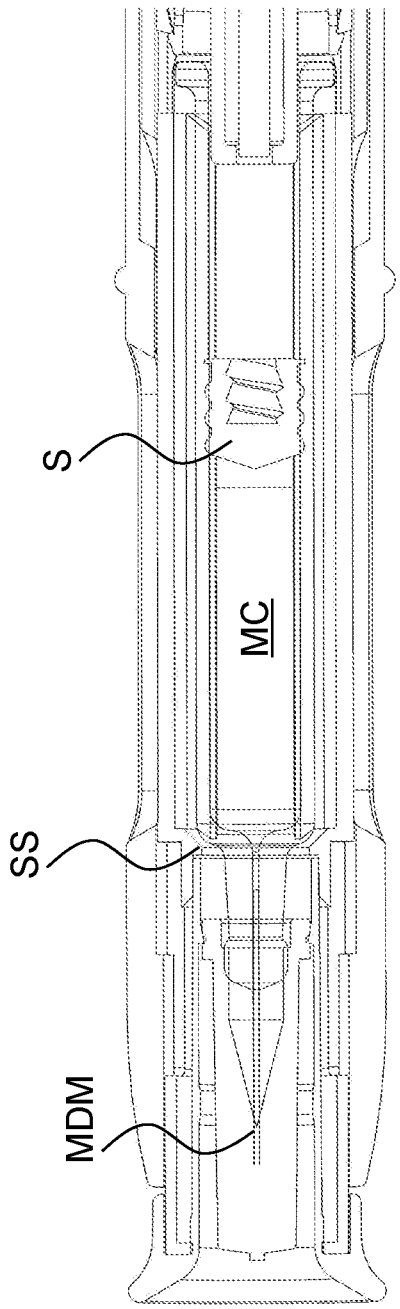

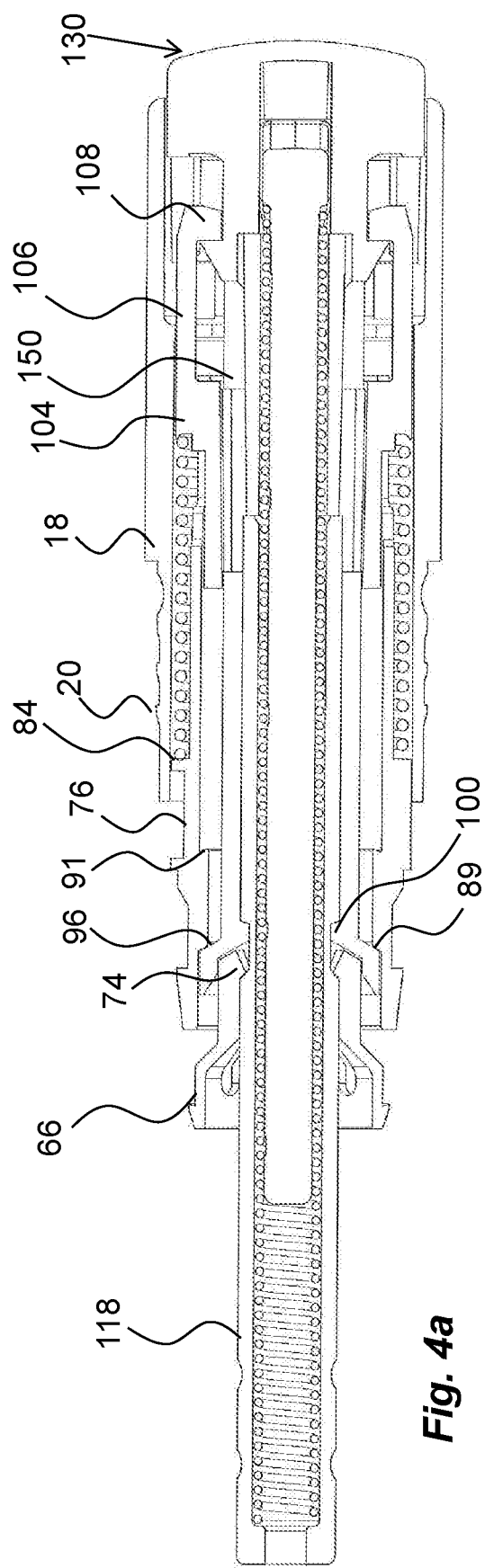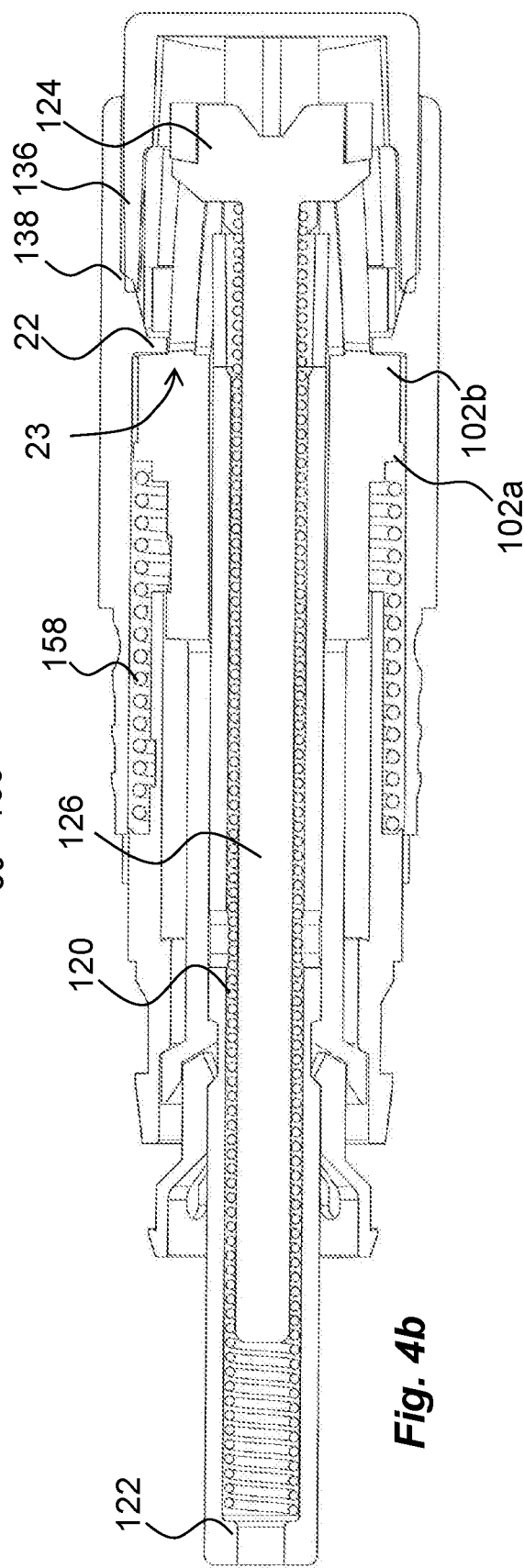
Fig. 4a
Fig. 4b

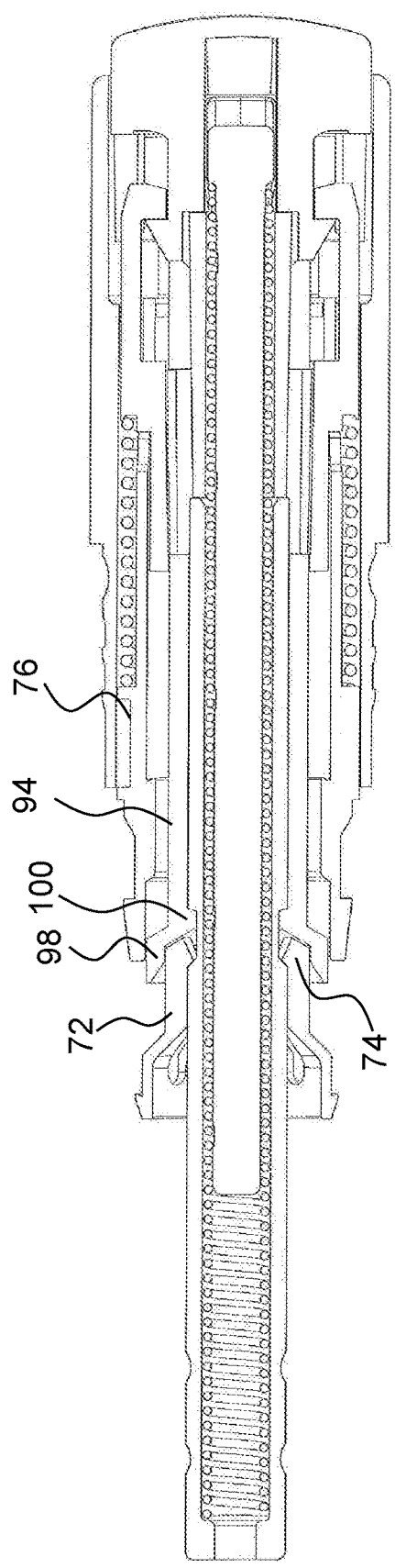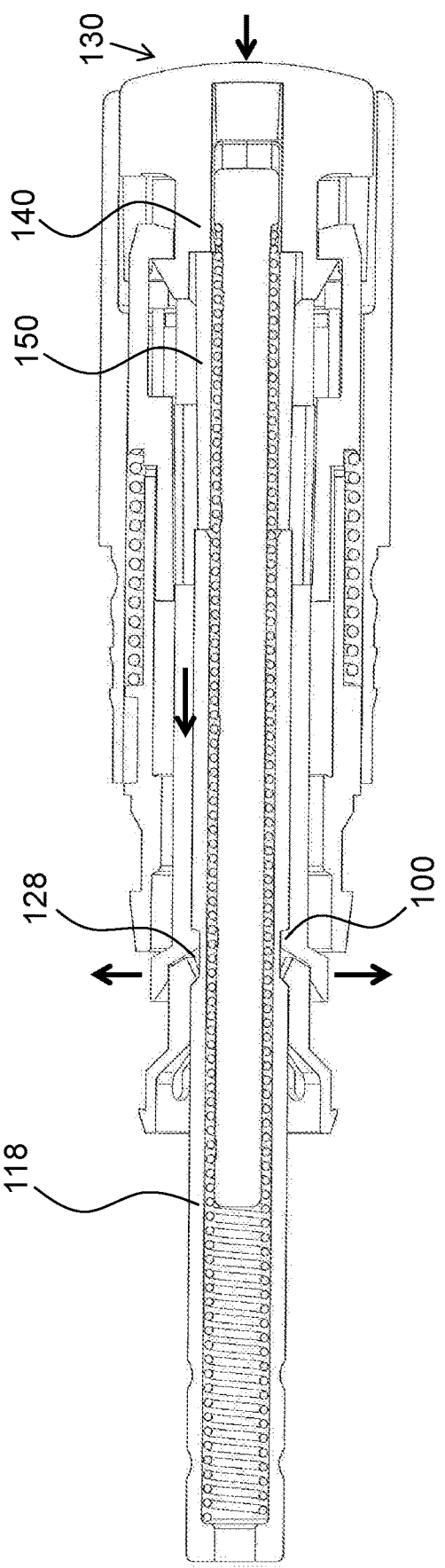
Fig. 10
Fig. 11

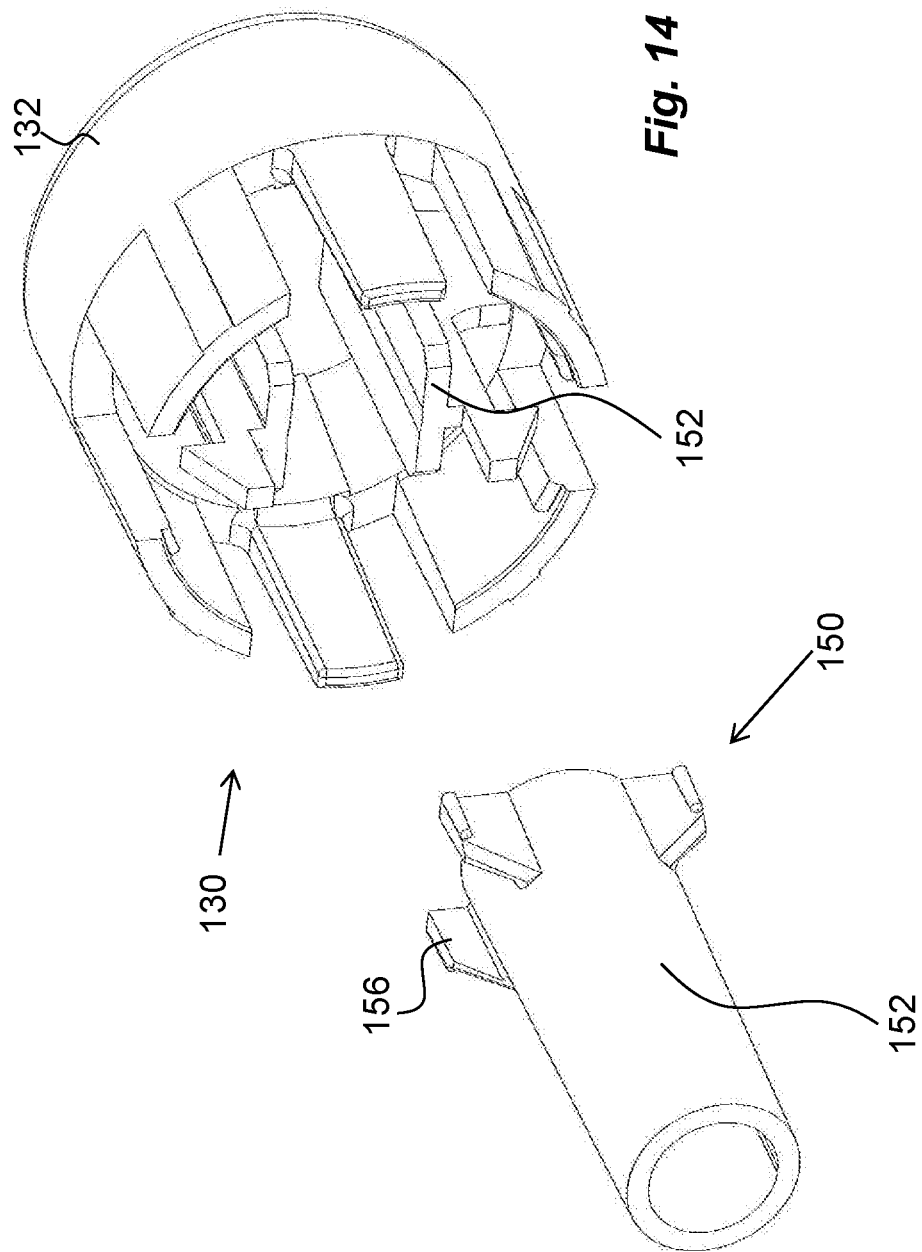

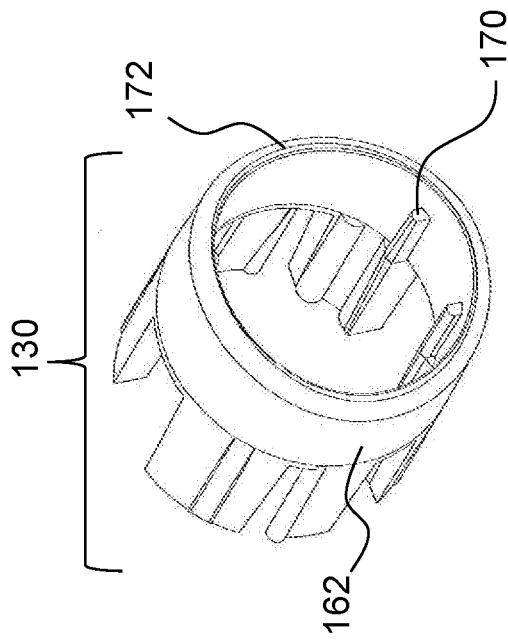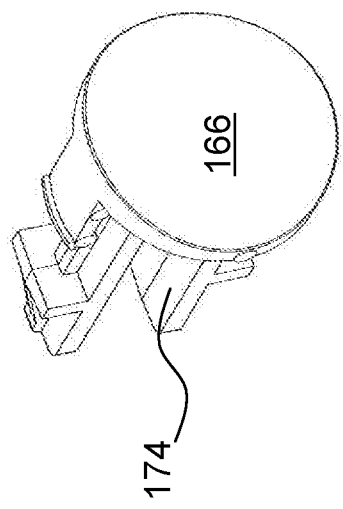
Fig. 16
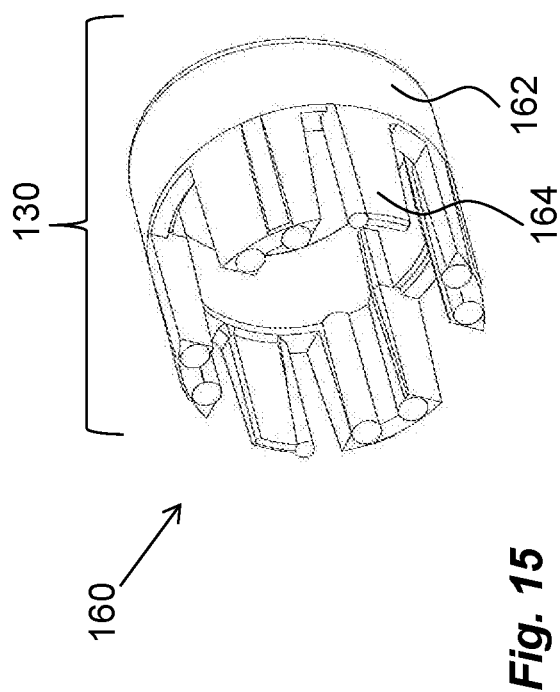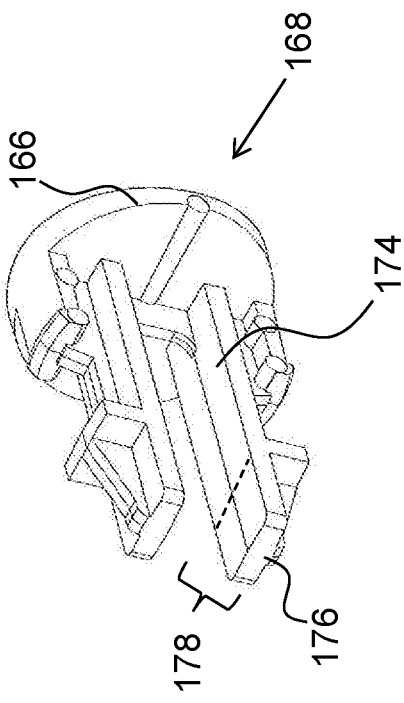
Fig. 15

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/076295 filed Nov. 1, 2016, which claims priority to Swedish Patent Application No. 1551550-5 filed Nov. 27, 2015. The entire disclosure contents of these applications are herewith incorporated by reference into the present application.

TECHNICAL AREA

The present disclosure relates to a medicament delivery device comprising a power unit with a specific activation mechanism.

BACKGROUND

A large number of medicament delivery devices for self-medication have been developed during the years, where many have a high degree of automatic functions and features in order to facilitate the use of the medicament delivery device, especially for unexperienced users.

One device that has gained a lot of attention on the market for its functionality is disclosed in the document WO 2011/005177 A1. The device disclosed therein has a number of automatic features like auto-penetration, auto-injection and automatic covering of the injection needle after removal of the medicament delivery device from the dose delivery site.

Even though working very well, the medicament delivery device according to WO 2011/005177 A1 comprises quite a lot of components that on the one hand provides an increased complexity regarding interaction between the components as well as increased assembly complexity and on the other hand increased manufacturing costs due to the number of components.

Further, there is an increased demand for medicament delivery devices that can handle medicament containers of different sizes, i.e. containing different volumes of medicament. One problem in that respect is that the length of the medicament container differs in that the position of a plunger rod when contacting a stopper that is movable inside a medicament container is different depending on the size of volume of the medicament to be delivered. Usually many parts of a medicament delivery device need to be redesigned in order to handle different medicament containers, including plunger rods, activation buttons and the like. It would be an advantage if the number of components could be kept as low as possible at the same time as the flexibility of the medicament delivery devices regarding handling of medicament container of different sizes could be improved.

SUMMARY

The aim of the present disclosure is to remedy the drawbacks of the state of the art medicament delivery devices and to provide a solution with a good functionality. The aim is solved by a medicament delivery device comprising the features of the independent patent claim. Preferable embodiments of the present disclosure form the subject of the dependent patent claims.

A medicament delivery device is presented having a housing, arranged to accommodate a medicament container as well as a power unit arranged inside the housing, wherein the medicament container is arranged with a movable stopper. Preferably the power unit may comprise a plunger rod, a drive spring operably arranged to act on the plunger rod wherein the plunger rod may be operably arranged to act on the medicament container. Further an actuator may be arranged, comprising holding elements, capable of releasibly holding the plunger rod with the drive spring in a tensioned state. An actuator sleeve may also be arranged to be operably connected to the actuator for releasibly locking the holding elements in a holding state.

According to a favourable solution, the medicament delivery device may further comprise a medicament delivery member guard slidably movable in the housing and arranged to act on the actuator sleeve for setting the holding elements with the actuator sleeve in a first activation state. Also, an activator unit may be arranged to be manually operated and which is operably connected to the plunger rod for setting the holding elements with the actuator sleeve in a second activation state, wherein the plunger rod is released when both activation states are set.

Preferably an adjuster element is operably arranged between the plunger rod and the activator unit, which adjuster element has a length chosen dependent on the initial position of the stopper in relation to the initial position of a proximal end of the plunger rod. In this manner, the same basic medicament delivery device may be used for different sizes of medicament containers and especially medicament containers with different lengths in the sense that the stopper then is positioned differently initially in relation to the support points or surfaces of the medicament container. In this context it is to be understood that the length is from a support surface of the medicament container in the proximal direction and a stopper.

This is shown in FIGS. 1a and 1b showing a state of the art medicament delivery device provided with medicament containers MC having different volumes. A stopper S may then have a different starting position depending on the volume of medicament that is to be administered from the MC through a medicament delivery member MDM. The MC has a support surface SS that is the same for all MC. Thus, the starting point where the proximal end of a plunger rod is positioned in contact with a stopper of a medicament container may be different depending on the length of the medicament container With the present disclosure, these differences may be handled by adjuster elements that can be replaced easily during assembly of the medicament delivery devices depending on the required medicament containers.

According to one possible solution, the drive spring may be arranged inside the plunger rod and in that respect the adjuster element may comprise a generally tubular member such that the drive spring extends through the adjuster element. The drive spring may buckle somewhat when tensioned, which may give rise to lateral forces on the plunger rod because it is arranged inside the plunger rod, and may also act on the adjuster element. For this reason, the adjuster element may comprise stabilizing elements arranged to prevent misalignment due to the lateral forces from the drive spring. In this respect the actuator sleeve may comprise guide surfaces arranged to interact with the stabilizing elements of the adjuster element.

According to one feasible solution, the activator unit may comprise a number of proximally extending posts, which posts are arranged with proximally directed surfaces in contact with said adjuster element. Further, the adjuster element may be a separate component that is replaced depending on the size of the medicament container to be used. As an alternative, the adjuster element may be integrated in the activator unit. In this case, the whole activator unit, or specific components of the activator unit is replaced depending on the medicament container to be used.

When the activator element is integrated in the activator unit and when the activator unit comprise a number of proximally extending posts, then the adjuster element may comprises a section of the posts directed in the proximal direction. Further, the activator unit may comprise locking elements arranged to cooperate with corresponding locking elements of the actuator sleeve for preventing movement of the activator unit in a distal direction. In that respect, the holding elements may comprise a number of tongues arranged with ledges arranged to engage recesses in the plunger rod.

Further, the actuator sleeve may be arranged slidable in relation to the actuator, wherein movement of the medicament delivery member guard in a distal direction causes the actuator sleeve to move distally to the first activation state.

These and other aspects of, and advantages with, the present disclosure will become apparent from the following detailed description of the disclosure and from the accompanying drawings.

BRIEF DESCRIPTION OF DRAWINGS

In the following detailed description of the present disclosure, reference will be made to the accompanying drawings, of which FIGS. 1a, 1b show a cross-sectional view of a state of the art medicament delivery device, with medicament containers having different volumes, FIG. 4 is a cross-sectional view of the power unit of FIG. 3, FIGS. 5-8 are detailed views of components comprised in the power unit of FIG. 3, and FIGS. 9-13 are cross-sectional view showing different functional states of the power unit of FIG. 3, and FIGS. 14-17 are detailed views of adjuster elements and activator units that may be comprised in the power unit of FIG. 3.

DETAILED DESCRIPTION

Figure 2:
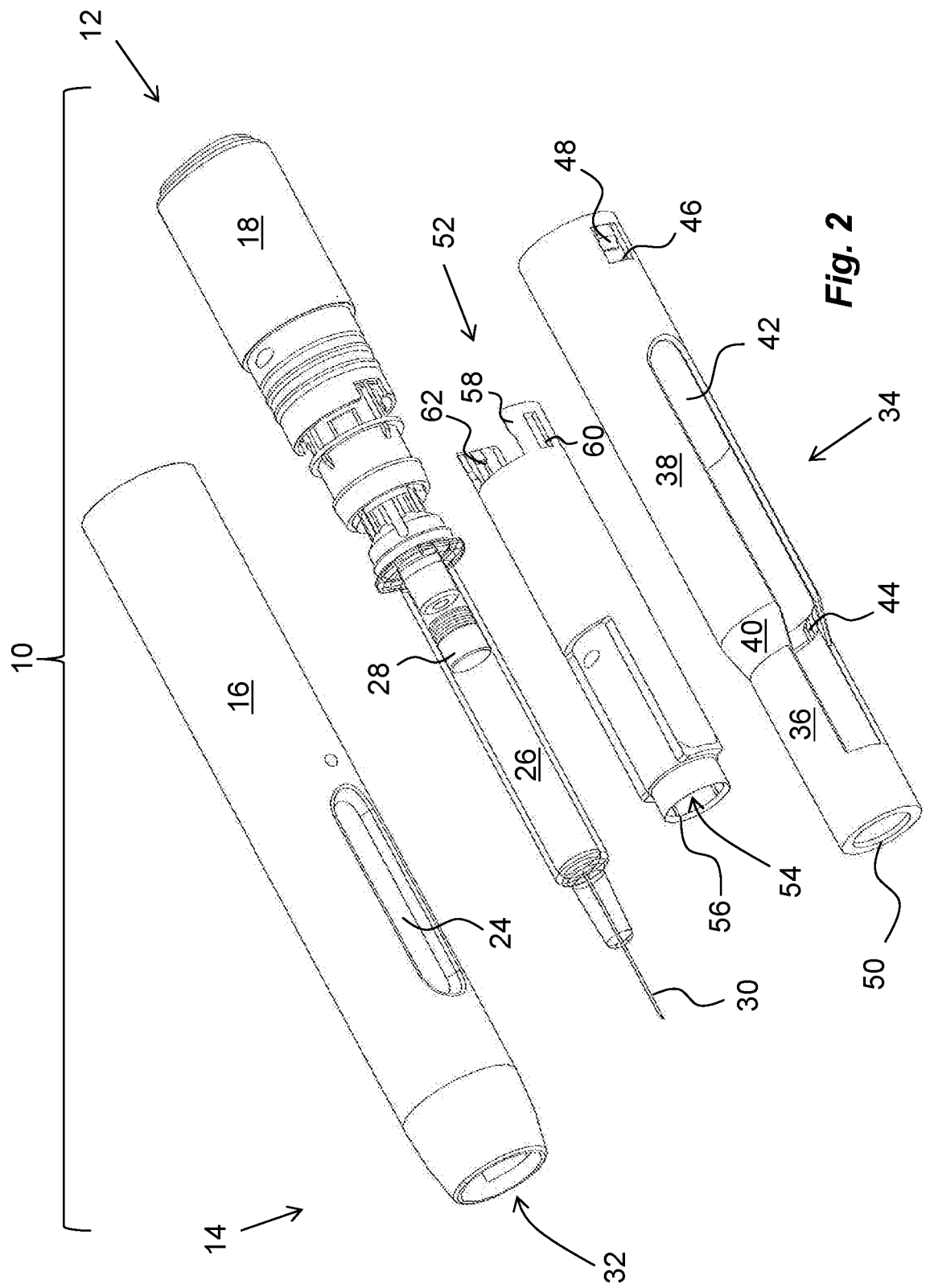
FIG. 2 shows an exploded view of an example of a medicament delivery device.

FIG. 2 shows an example of an embodiment of a generally elongated medicament delivery device 10 comprising the present disclosure and having a distal end 12 and a proximal end 14. The medicament delivery device 10 is provided with an elongated housing, comprising a proximal housing part 16 and a distal housing part 18. The distal end of the proximal housing part 16 is arranged with engagement means (not shown) such as annular recesses e.g. on its inner surface adapted to interface with corresponding engagement means 20, FIG. 4a, on e.g. the proximal outer surface of the distal housing part 18. The distal housing part 18 is further arranged with a central wall 22, FIG. 4b, which wall 22 is provided with a central passage 23.

The proximal housing part 16 is arranged with elongated openings 24 for viewing a medicament container 26, FIG. 2. The medicament container 26 is arranged with a movable stopper 28 and a medicament delivery member 30. In the embodiment shown, the medicament delivery member 30 is integrated in the medicament container 26, but it is to be understood that the medicament delivery member 30 may be an attachable member wherein the attachment elements may be threads, bayonet fittings or luer-couplings, just to mention a few.

The proximal housing part 16 is further arranged with a central passage 32 through which a medicament delivery member guard 34 can extend. The medicament delivery member guard 34 comprises a first proximal part 36 having a certain diameter and a second distal part 38 having a diameter larger than the proximal part, where these parts are joined by an intermediate conical part 40, FIG. 2. Two elongated slits 42 are arranged along the medicament delivery member guard 34, on opposite sides thereof, for viewing the medicament container 26. On an inner surface of the conical part 40 a ledge 44 is arranged.

Further, at the distal end of the medicament delivery member guard 34 two openings 46 are arranged opposite each other, where each opening 46 is arranged with a proximally directed, somewhat inwardly projecting, flexible, tongue 48, FIG. 2. The medicament delivery member guard 34 is further arranged with a central opening 50 at its proximal end, through which the medicament delivery member 30 may protrude as will be described.

A generally tubular medicament container holder 52 is slidably and coaxially arranged inside the medicament delivery member guard 34. The proximal part of the medicament container holder 52 is arranged with a central passage 54 through which the medicament delivery member 30 may protrude. The central passage 54 is further arranged with an annular support surface 56. The support surface 56 is arranged to cooperate with a neck portion of the medicament container 26 providing a support and reference position for the medicament container 26. The distal end of the medicament container holder 52 is arranged with two distally extending tongues 58, where each tongue is arranged with an opening 60 and an inwardly directed ledge 62 on the distal edge of each opening, FIG. 1.

The medicament delivery device further comprises a power unit 64, FIGS. 3-6. The power unit 64 comprises a holding element 66. It comprises a ring-shaped body 68, FIG. 5, having an annular ledge 70 arranged around its circumference and a number of flexible tongues 72 directed towards the distal end of the device and wherein each tongue 72 is arranged with radially inwardly directed ledges 74, FIG. 6. The holding element 66 is intended to interact with the container holder 52 as will be described below. The power unit 64 further comprises an actuator sleeve 76, FIG. 5, which is slidably and coaxially arranged to the housing and connected to the medicament delivery member guard 34 as will be described below.

Figure 5:
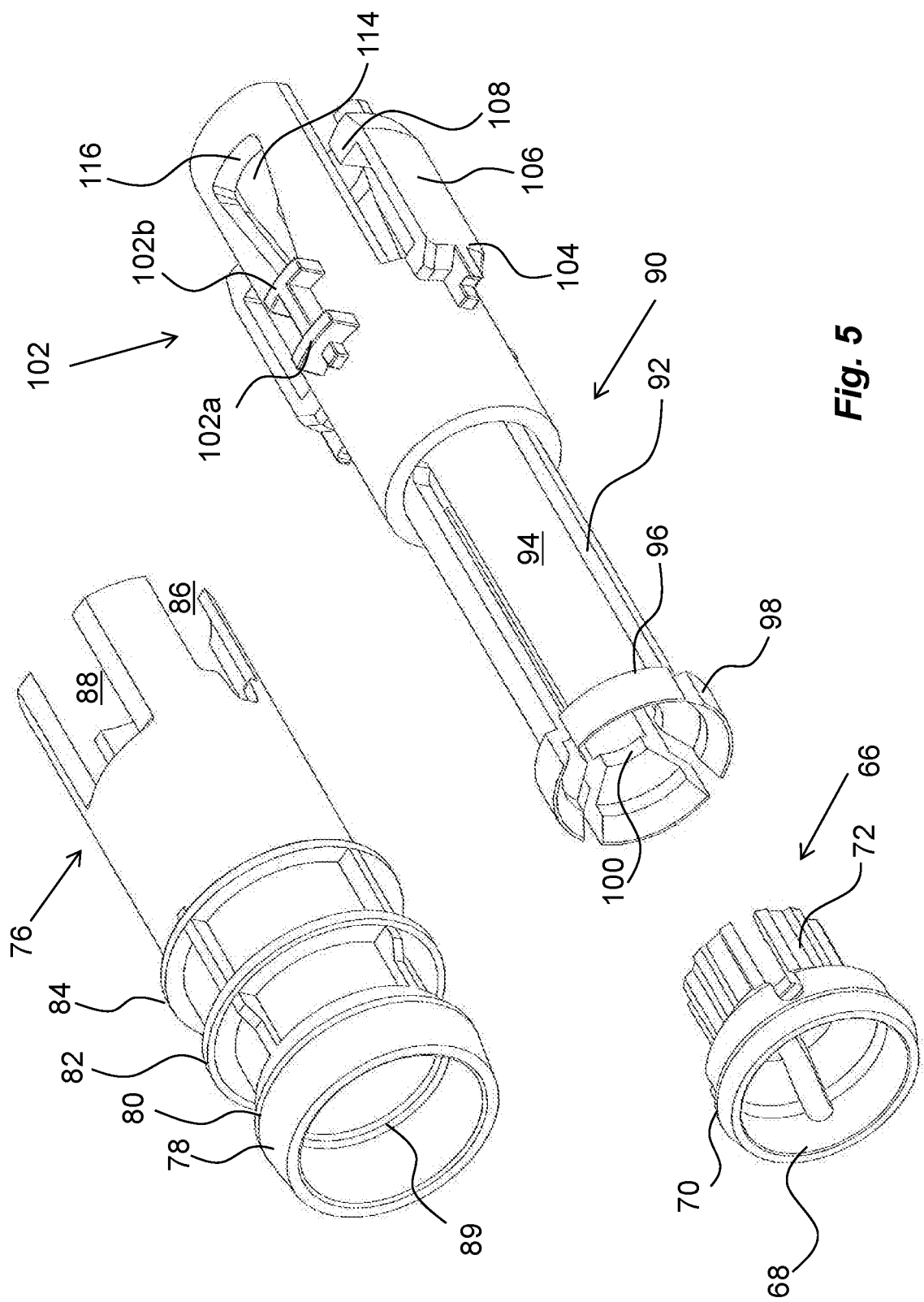

The actuator sleeve 76 has a tubular shape and comprises a proximal end with a conical part 78 ending in a ledge 80 on its outer surface. At a distance from the ledge 80, a first annular ring 82 is arranged on the outer surface. A second annular ring 84 is also arranged a further distance from the ledge 80. The distal end of the actuator sleeve 76 is arranged with at least two oppositely arranged first cut-outs 86 of a generally rectangular shape. The distal end of the actuator sleeve 76 is further arranged with two oppositely arranged second cut-outs 88. An annular, proximally directed, ledge 89, FIG. 5, is arranged on the inner surface of the actuator sleeve 76. The actuator sleeve is further arranged with a distally directed, annular, ledge 91, FIG. 6.

Figure 6:
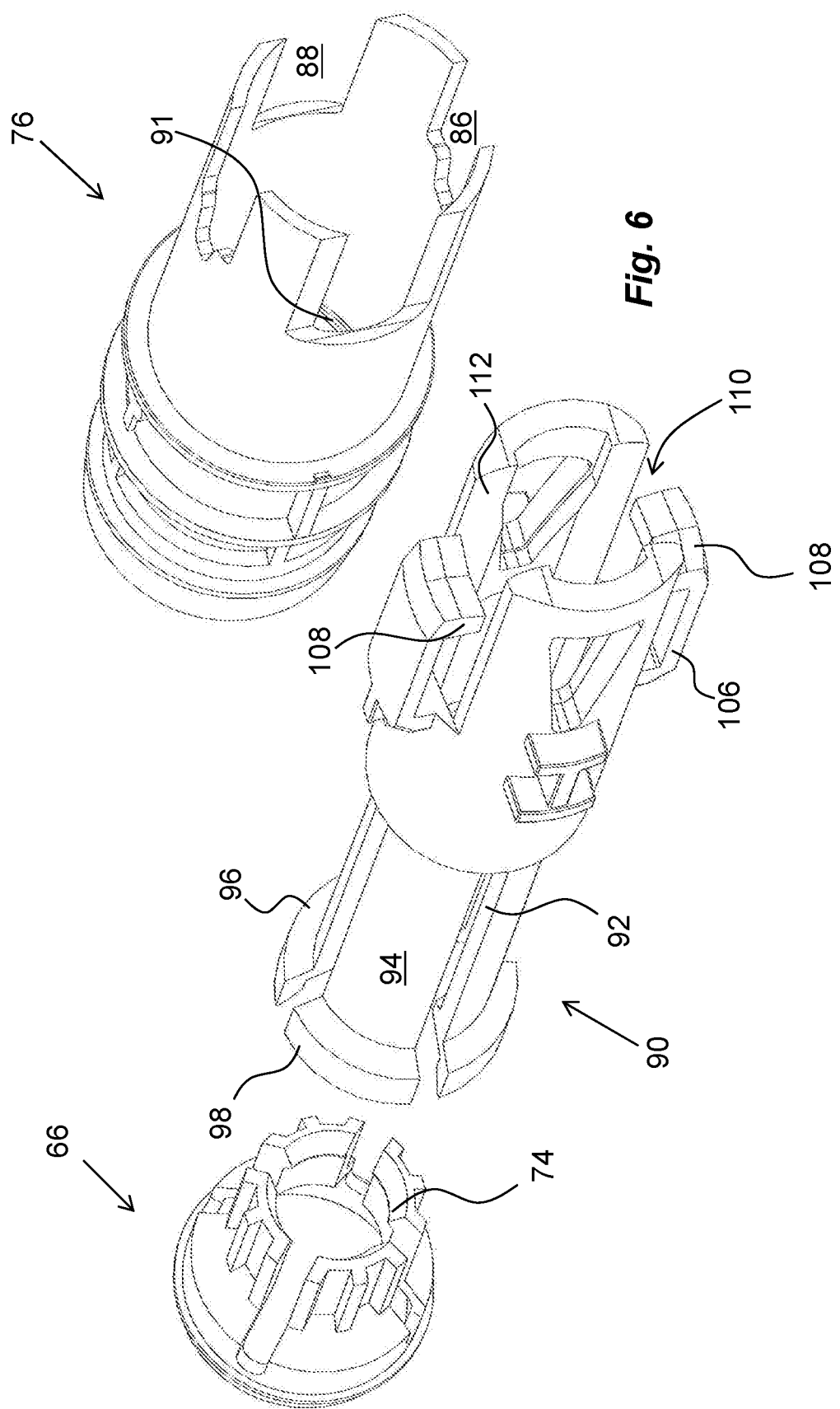

A generally tubular actuator 90 is slidaby and coaxially arranged to the actuator sleeve 76, FIGS. 5 and 6. The actuator comprises a number of longitudinally directed cut-outs 92 that are arranged at the proximal end of the actuator 90 so as to form flexible tongues 94. The proximal end of each flexible tongue 94 has an inclined transition surface 96 which meets with a band-shaped part 98 with enlarged diameter. On the inner surface adjacent the transition surface 96 an annular inwardly directed ledge 100 is arranged, FIG. 5. The tongues 94 with the ledges 100 form holding elements as will be described.

The actuator 90 is also provided with two oppositely arranged stop elements 102 directed radially outwards from the outer surface on either side and having a proximally directed ledge 102a, where the width of said proximally directed ledge 102a correspond to the width of the second cut-outs 88 of the actuator sleeve 76, FIG. 5. The stop elements 102 further have a distally directed ledge 102b, the function of which will be described below. The stop elements 102 are arranged to fit into the second cut-outs 88. The actuator 90 is further provided with at least two oppositely positioned ledges 104 directed radially outwards from the outer surface on either side arranged to mate the first cut-outs 86 of the of the actuator sleeve 76.

Further, the ledges 104 extend in the distal direction and are transformed into generally radially flexible arms 106, where the free ends of the arms are arranged with inwardly directed ledges 108 functioning as locking elements as will be described. The actuator 90 is further arranged with slits 110, FIG. 6, extending from the distal end towards the proximal end forming parallel side surfaces 112 that will act as guide surfaces as will be described. The slits are positioned radially inwards of the flexible arms. Further, the distal end of the actuator 90 is arranged with cut-outs 114, which form proximally directed support surfaces 116, the function of which will be described below.

Figure 3:
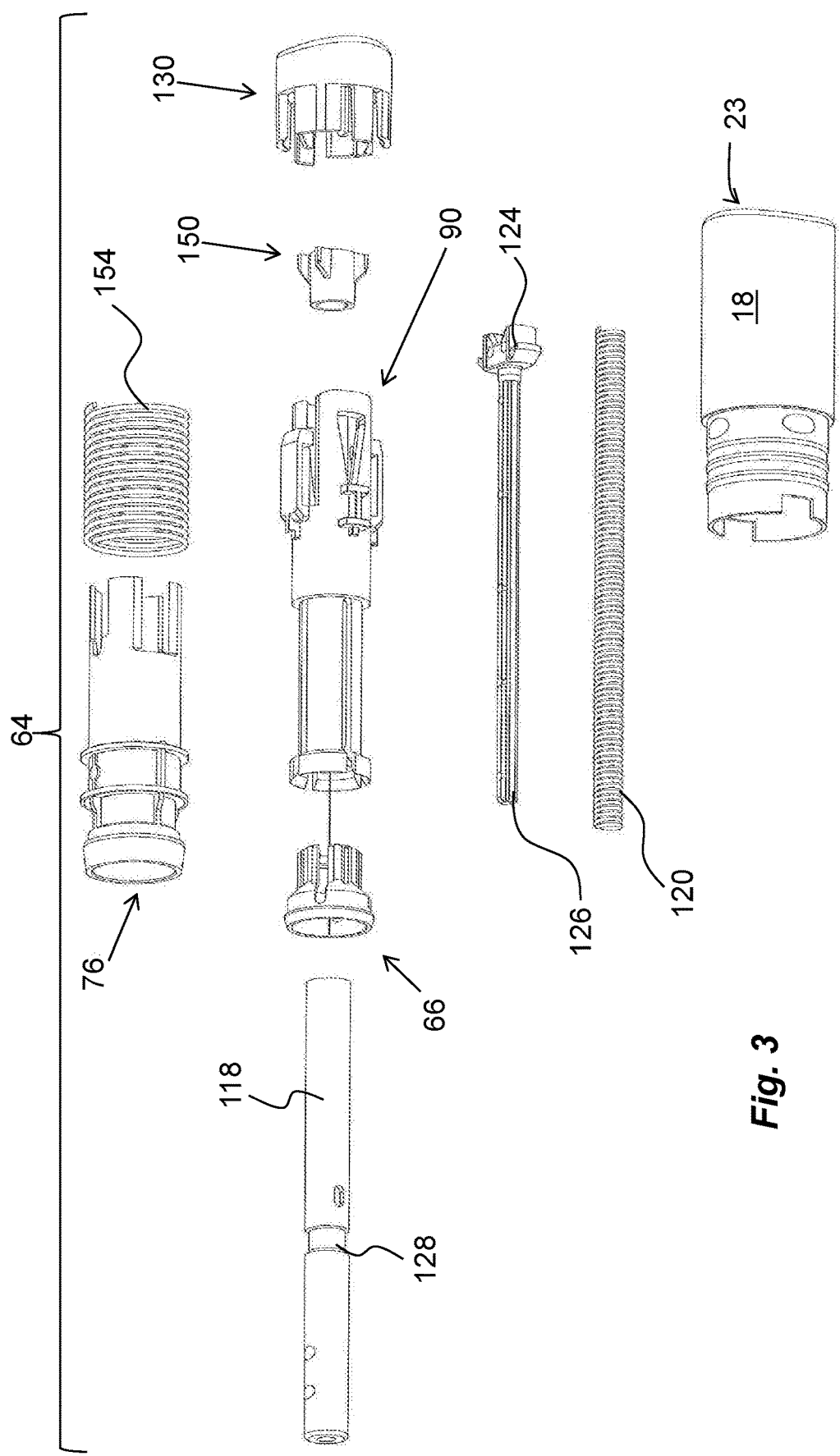
FIG. 3 shows an exploded view of a power unit comprised in the medicament delivery device of FIG. 1.

The power unit 64 further comprises a plunger rod 118 arranged to act on the stopper 28 of the medicament container 26, FIG. 3. A drive spring 120 that in the embodiment shown is a compression spring is arranged inside the plunger rod 118 between a proximal wall 122 of the plunger rod 118, FIG. 4b, and a proximally directed support surface of generally radially directed ledges 124 arranged in a distal area of an elongated guide rod 126, which is extending through the drive spring 120. The ledges 124 of the guide rod 126 are arranged to fit inside the cut-outs 114 and engage with the support surfaces 116 of the actuator 90. The plunger rod 118 is arranged with a number of recesses that in the embodiment shown is a circumferential groove 128 with a certain width, wherein the annular inwardly directed ledge 100 of the actuator 90 and the radial inwardly directed ledges 74 of the holding element 66 fit into the groove 128, FIG. 4. It is to be understood that the groove 128 may be replaced with a number of discrete recesses or cut-outs.

Figure 7:
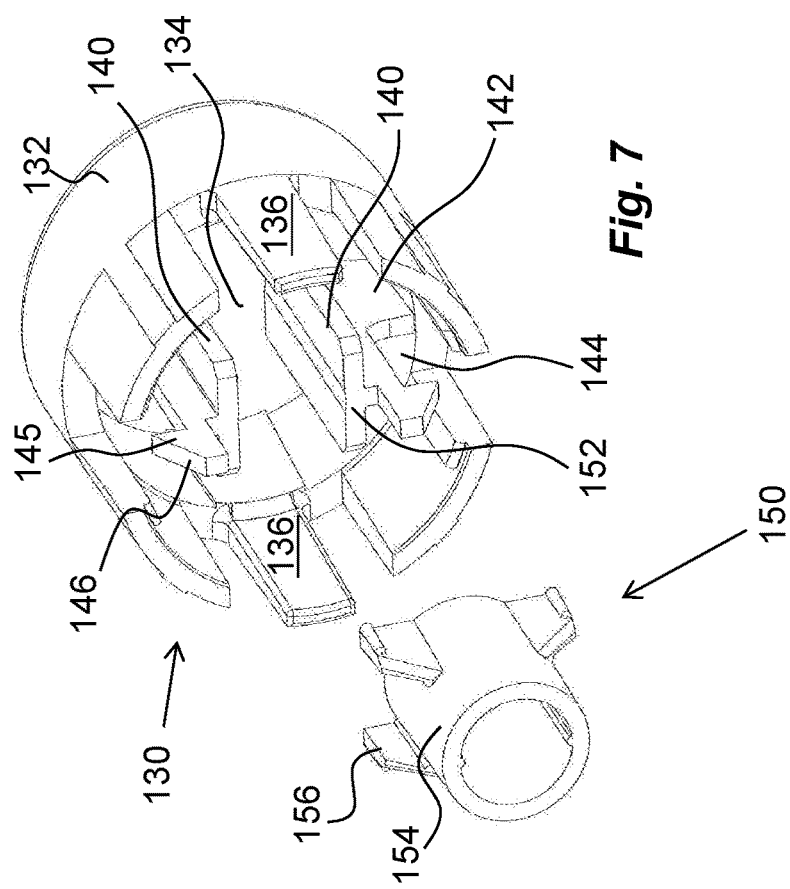
Figure 8:
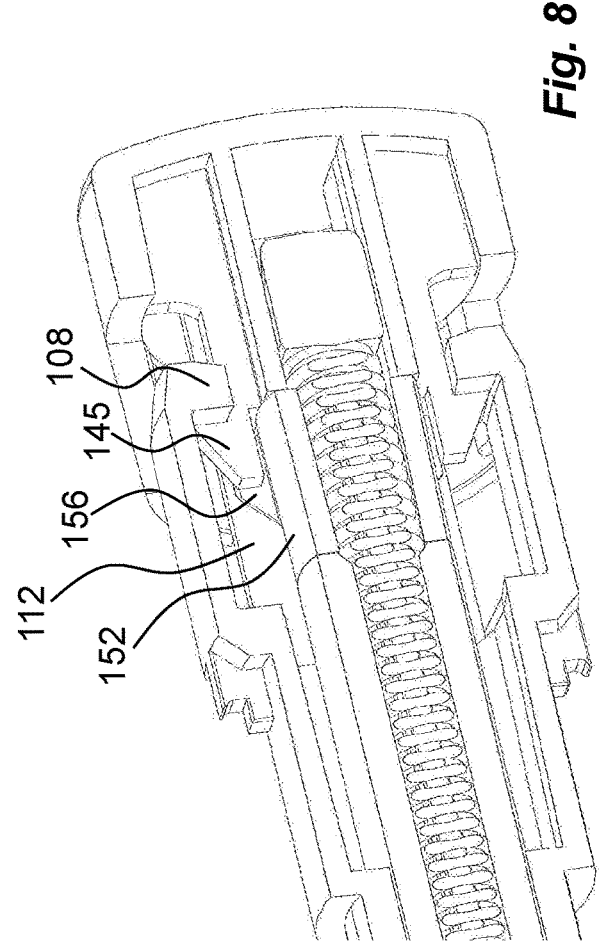

A manually operated activator unit 130, e.g. a push button, has a distal portion protruding distally from the distal housing part 18 through the central passage 23 thereof. In the embodiment shown the activator unit 130 comprises a generally tubular body 132, FIG. 7, provided with a transversal end wall 134. A proximally directed edge of the tubular body 132 is arranged with proximally directed tongues 136, which tongues 136 are flexible in a generally radial direction. These tongues are to interact with inclined surfaces 138, FIG. 4b, on the inner surface of the distal housing part 18, as will be described below.

The transversal end wall 134 is further arranged with proximally directed posts 140 that have a generally T-shape in cross-section. At the proximal end of the posts, the web 142 of the T is arranged with a cut-out 144, thereby forming a distally directed locking element 145 as will be described. Further, the edge surface of the web 142 of the T is arranged with a bevel 146.

According to the disclosure an adjuster element 150, FIGS. 3 and 7, is arranged between the distal end of the plunger rod 118 and a proximally directed surface 152 of the posts 140. The adjuster element 150 is formed as a generally tubular body 154 arranged with an inner diameter that generally corresponds to the inner diameter of the plunger rod 118 such that the drive spring 120 may fit there through as seen in FIG. 3. The adjuster element 150 is further arranged with stabilizing elements that in the embodiment shown comprises four flat ledges 156 extending in the longitudinal direction, wherein two ledges 156 are arranged parallel to each other and extend in one direction from the tubular body while the other two ledges also are parallel to each other and extend in an opposite direction. A distance is then created between the ledges of the pairs such that when the adjuster element 150 is arranged in the power unit 88, the body 154 of the adjuster element 150 fits between the distal end of the plunger rod 118 and the proximally directed end surfaces 152 of the T-shaped posts 140 wherein the pairs of ledges 156 are designed to fit into the slits 110 of the actuator 90 and to be in contact with the guide surfaces 112 to provide guides against misalignment of the adjuster element 150 due to possible buckling forces from the drive spring 120.

The device further comprises a medicament delivery member guard spring 158, coaxially arranged on the actuator sleeve 76. The annular proximal end of the medicament delivery member guard spring 154 is arranged resting on the second annular ring 84 of the actuator sleeve 76, FIGS. 4a and 4b, and the annular distal end of the medicament delivery member guard spring 154 is arranged resting on the proximal surfaces of the stop ledges 102 and 104 of the actuator 90, FIG. 4.

The disclosure is intended to function as follows. When the power unit 64 is to be assembled, the guide rod 126 is pushed into the actuator 90 from the distal end until the ledges 124 of the guide rod 126 are snapped into the cut-outs 114 of the actuator 90. The actuator sleeve 76 with the medicament delivery member guard spring 154 is pushed onto the actuator 90 until the ledges 102, 104 of the actuator enter the cut-outs 86, 88 of the actuator sleeve 76, preventing further movement. In this position the medicament delivery member guard spring 154 is tensioned and the tongues 94 of the actuator 90 may flex in the generally radial direction. The drive spring 120 is then entered into the plunger rod 118 and the drive spring 120 and plunger rod 118 are pushed into the actuator 90 from the proximal direction, flexing the tongues 94 in the radial direction until the ledges 100 of the tongues 94 enter the annular groove 128, at the same time tensioning the drive spring 120.

The holding element 66 is pushed onto the plunger rod 118 from the proximal direction until the ledges 74 of the holding element 66 also engage with the annular groove 128 of the plunger rod 118 and are positioned radially inwards of the tongues 94 of the actuator 90. Then the actuator sleeve 76 is pushed in the proximal direction onto the actuator 90, thereby preventing the ledges 100 of the tongues 94 of the actuator 90 as well as the ledges 74 of the holding element 66 from escaping the annular groove 128 of the plunger rod 118.

This assembly is then pushed into the distal housing part 18 from the proximal direction and stop when the distally directed stop ledge 102b contacts the central wall 22 as seen in FIG. 4b. The adjuster element 150 is then entered at the distal end of the actuator where the ledges are in contact with the side surfaces of the slits. The activator unit 130 is then pushed inside the distal housing part from the distal direction. When pushed inside, the ledges 108 of the arms 104 will come in contact with the bevelled surfaces 146 of the posts 140 whereby the arms 104 will flex outwardly in the radial direction until the ledges 108 enter the cut-outs 144 of the posts 140, thereby preventing movement of the actuator 90 in the proximal direction by the locking elements 145. Further, the actuator sleeve 76 is pushed in the proximal direction, but is prevented from movement in the proximal direction due to the ledge 89 on the inner surface of the actuator sleeve 76 abutting the inclined transition surface 96 of the actuator 90 as seen in FIG. 4a.

When the device is to be used, a medicament container 26 is placed in the container holder 52 and the assembly is placed in the proximal housing part 16. The distal housing part 18 with the power unit 64 is then interconnected and locked to the proximal housing part by the attachment elements 20. Further, the inwardly directed ledges 62 at the distal end of the medicament container holder 52 engage with the annular ledge 70 of the holding element 66, interconnecting them. The device is now ready to use. Also the distal part of the medicament delivery member guard 34 will surround the actuator sleeve 76 wherein the inclined tongues 48 will pass the ledge 80 providing a lock in the longitudinal direction of between the medicament delivery member guard 34 and the actuator sleeve 76. Also a distal end surface of the medicament delivery member guard 34 is in contact with the first annular ring 82.

Figure 9:
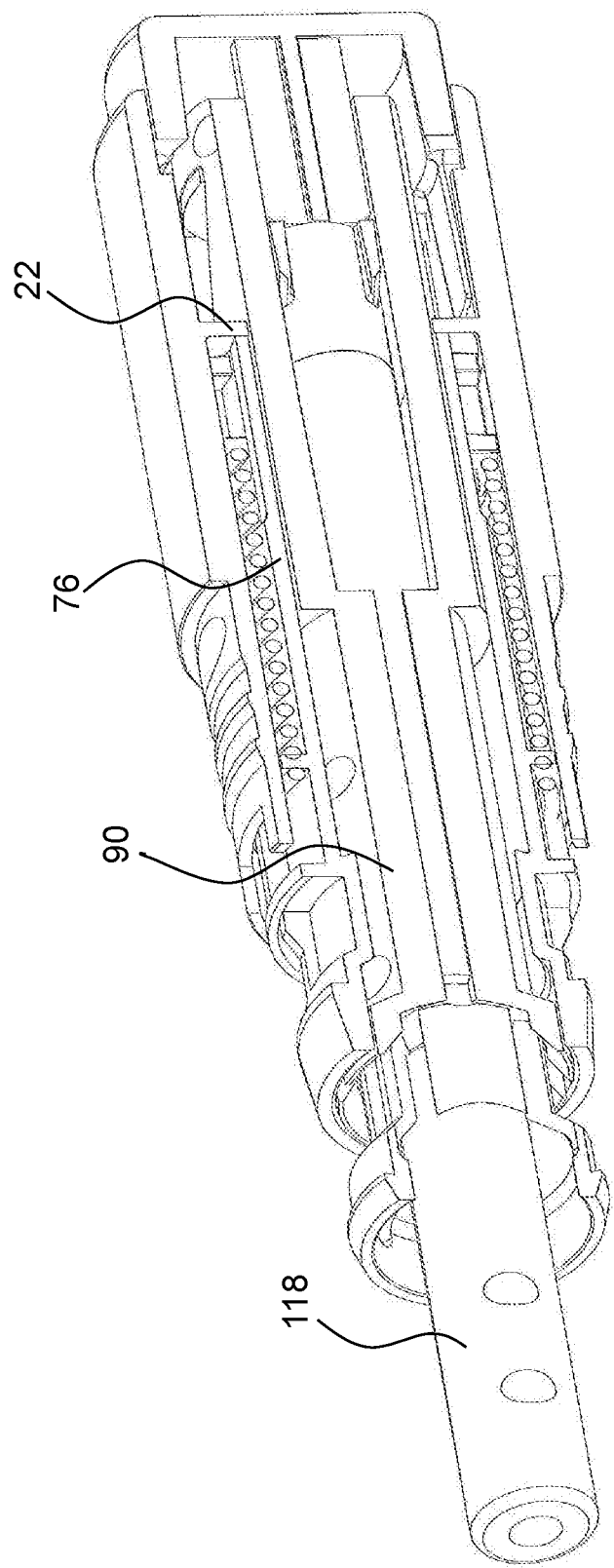

When the medicament delivery device is to be used, the proximal end of the medicament delivery device 10 and thus the medicament delivery member guard 34 is pressed against a dose delivery site. Now the medicament delivery device 10, apart from the stationary medicament delivery member guard 34 and the inter-connected actuator sleeve 76, is moved in the proximal direction until the distal end of the actuator sleeve 76 comes in contact with the central wall 22 of the distal housing part 18, FIG. 9, wherein the movement is stopped.

The movement of the actuator 90 in relation to the actuator sleeve 76 has caused the band-shaped part 98 to protrude to some extent out of the proximal end of the actuator sleeve, FIG. 10, setting the power unit in a first activation state. The user may now press on the activator unit 130 in the proximal direction. At first the free ends of the tongues 136 of the activator unit 130 will hit the ledge 138 of the distal housing part 18 providing a tactile feeling of resistance, also functioning as a resistance against unintended activation. Further pressing on the activator unit 130 will cause the tongues 136 to flex inwards, allowing the activator unit 130 to move in the proximal direction. Now the proximally directed posts 140 will act on the distal end of the adapter element 150, which in turn will act on the distal end of the plunger rod 118 and push the plunger rod 118 in the proximal direction, setting the power unit 64 in the second activation state.

Because of the engagement of the actuator 90 with its ledges 100 in the annular groove 128 of the plunger rod 118, also the actuator 90 will move in the proximal direction, FIG. 11. This movement will cause the band-shaped part 98 to be moved completely out of the actuator sleeve 76, FIG. 11, and because of the resilient properties of the tongues 94 of the actuator 90, the ledges 100 will move out of the annular groove 128 of the plunger rod 118, thereby releasing the plunger rod 118, which is due to that both activation states have been set.

If for instance the medicament delivery device 10 would be removed from the dose delivery site, then the first activation state is removed. If now the activator unit 130 is pressed, the plunger rod 118 together with the actuator 90 will move proximally in relation to the actuator sleeve 76 to the second activation state, but because the actuator sleeve 76 has not been pushed distally by the medicament delivery member guard 34, the first activation state is not set and the plunger rod 118 will not be released.

Due to the force of the drive spring 120, the plunger rod 118 is urged in the proximal direction. Since the ledges 74 of the holding element 66 are still in the annular groove 128 and the holding element 66 is connected to the medicament container holder 52, the medicament container holder 52 and the medicament container 26 with its medicament delivery member 30 will be moved in the proximal direction, when the plunger rod 118 is moved in the proximal direction, causing a penetration of the medicament delivery member 30 into the tissue of the patient. The movement of the medicament container holder 52 and the medicament container 26 is stopped when the proximally directed surfaces surrounding the neck portion 54 abut the ledge 44 on the inner surface of the medicament delivery member guard 34. It may also be that the force of the drive spring 120 will urge the plunger rod 118 in the proximal direction with such a force that the ledges of the holding element are forced out of the annular groove 128. However, since the plunger rod 118 is acting on the stopper 28 and due to the incompressibility of the medicament inside the medicament container 26 as well as the small passage in the medicament delivery member 30, the medicament container 26 with its container holder 52 will be moved in the proximal direction causing a penetration of the medicament delivery member 30 into the tissue of the patient.

Figure 12:
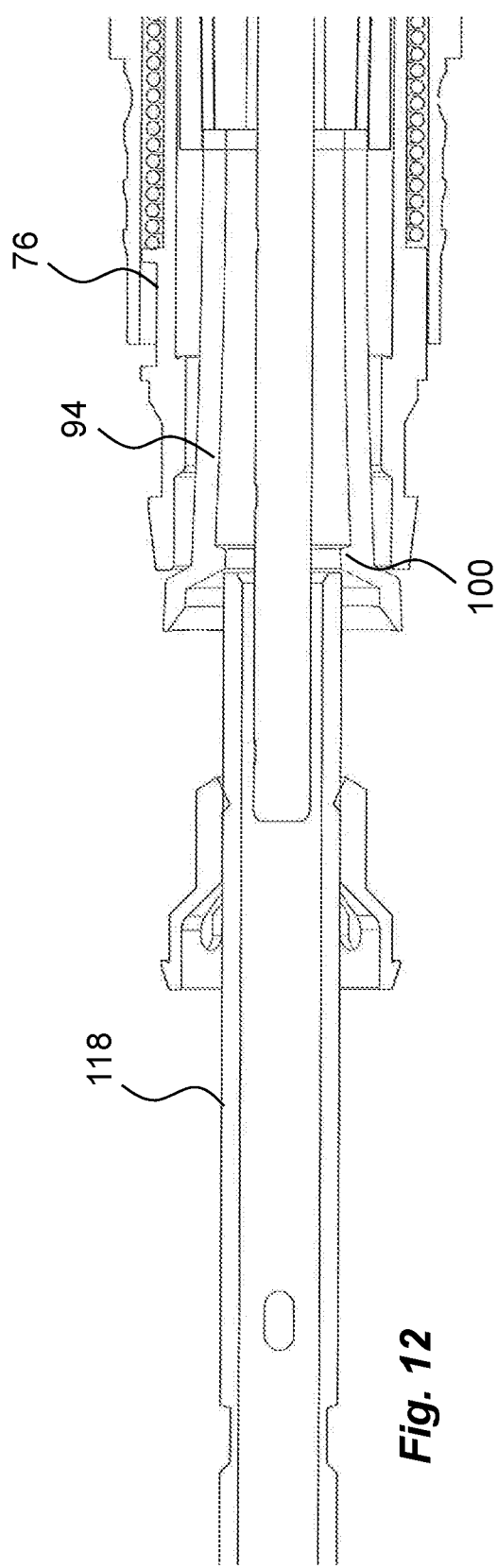

The plunger rod 118 is urged further in the proximal direction wherein the ledges 74 of the holding element 66 will be forced out of engagement with the annular groove 128 due to the flexing properties of the tongues 72 of the holding member. The plunger rod 118 will now act on the stopper 28 inside the medicament container 26, whereby a dose of medicament will be expelled through the medicament delivery member 30. When the plunger rod 118 has come to its most proximal position with the stopper 28 at the proximal end of the medicament container 26, an end-of-dose signal mechanism will be activated in that the distal end of the plunger rod 118 has passed the ledges 100 of the actuator 90, FIG. 12, whereby the tongues 94 of the actuator 90 can flex back radially inwards, which tongues 94 previously have had the additional function of acting as lock/release elements for the actuator 90. Due to the residual force of the drive spring 120, with its distal end acting on the ledges 124 of the guide rod 126, and since the ledges 124 of the guide rod 126 are engaging the actuator 90, the actuator 90 will move suddenly in the distal direction. This will cause the distally directed ledge 102b of the actuator 90 to hit the central wall 22 of the distal housing part 18, producing an audible and tactile signal that the dose delivery sequence is completed.

Figure 13:
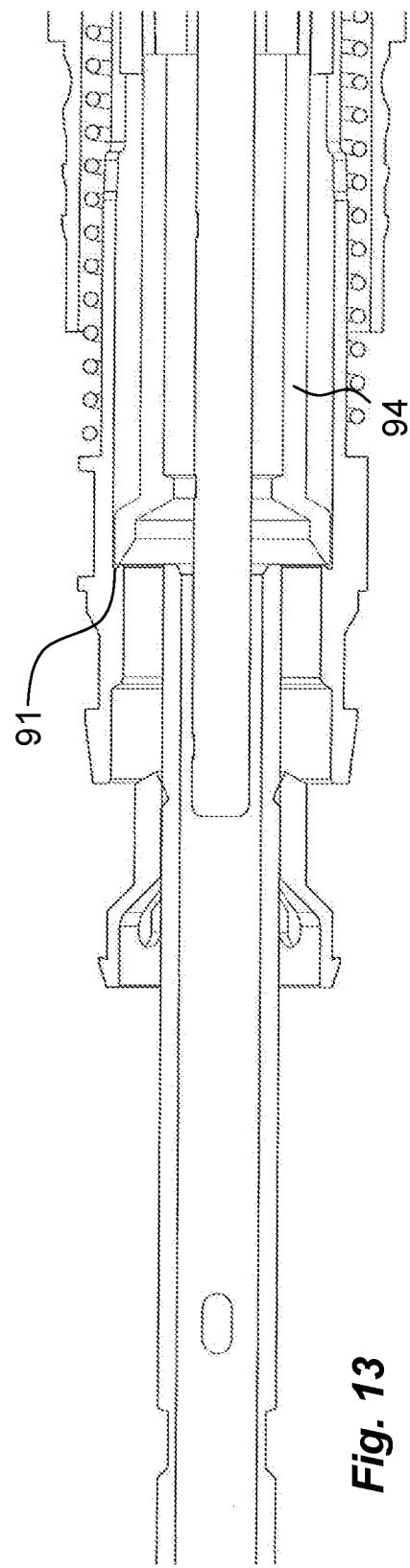

The user may now remove the medicament delivery device from the dose delivery site. This will cause actuator sleeve 76 and the medicament delivery member guard 34 to be moved in the proximal direction due to the force from the medicament delivery member guard spring 158 acting on the actuator sleeve 76 and because of the connection between the actuator sleeve 76 and the medicament delivery member guard 34, which movement will cause the medicament delivery member 30 to be shielded. In the extended position, the medicament delivery member guard 34 is locked because when the actuator sleeve 76 is moved in the proximal direction by the medicament delivery member guard spring 158, the band-shaped part 98 of the tongues 94 of the actuator 90 will pass the distally directed annular ledge 91 and flex in the radial direction, FIG. 13, whereby the tongues 94 will have the additional function of comprising a medicament delivery guard locking mechanism. This will cause an audible as well as tactile signal that the medicament delivery member guard 34 is locked. Thus, the arms 94 will also have the additional function of acting as a medicament delivery member guard locking signal mechanism. The lock will prevent any attempt to push the medicament delivery member guard 34 in the distal direction due to the band-shaped part 98 abutting the ledge 89. The device is now safe to discard.

According to the present disclosure the adjuster element 150 may be modified depending on the length of the medicament container used, and thus the dose size to be administered. As seen in FIG. 14, a longer adjuster element 150 than in the previous embodiment has been utilized when the medicament delivery device is to handle a shorter medicament container. As seen in the FIG. 14, the body 152 of the longer adjuster element is also arranged with guide ledges 156 for ascertaining the proper alignment and position in relation to the plunger rod 118 and to counter-act forces from the drive spring 120.

Figure 17:
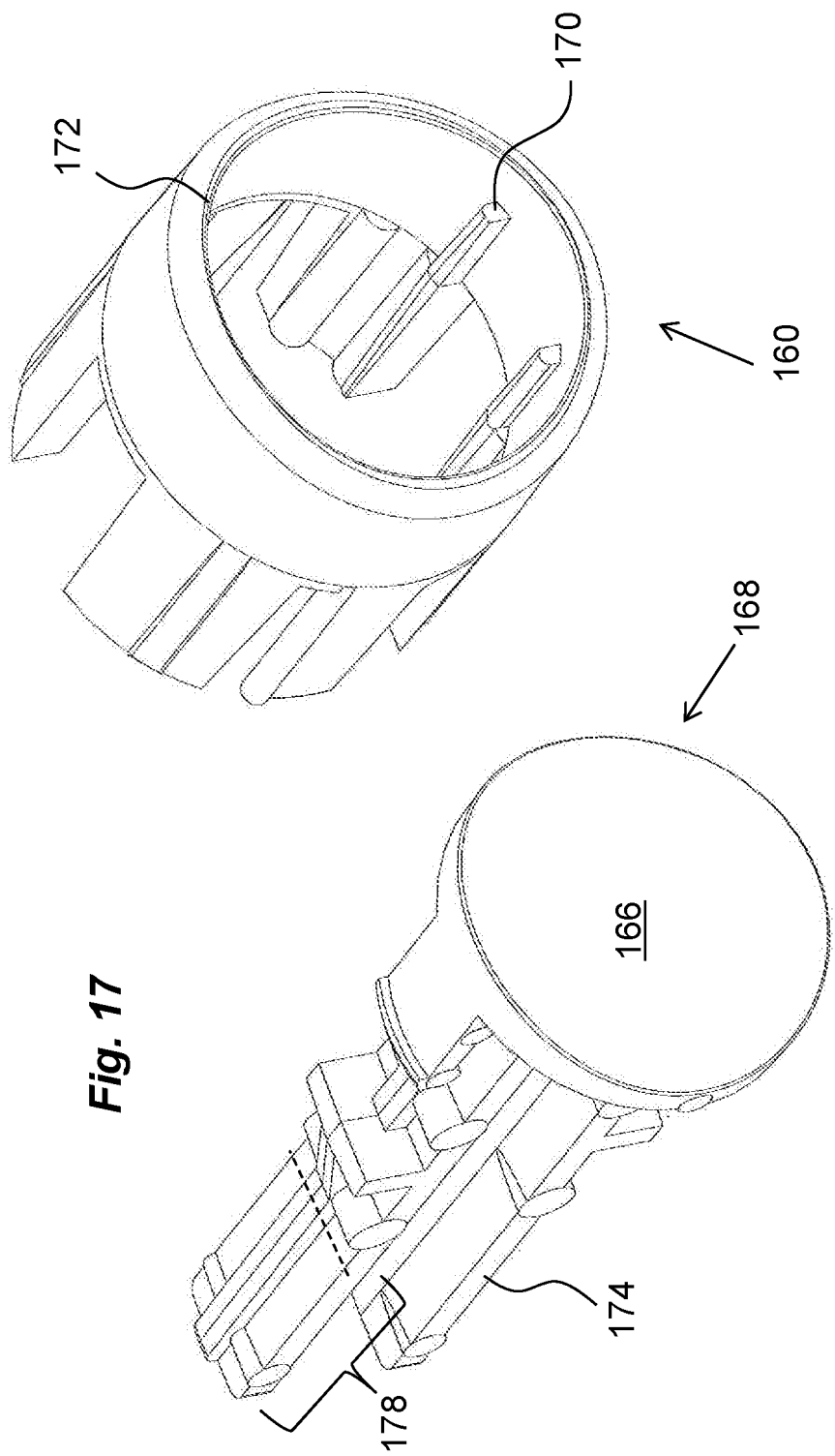

Another example of the present disclosure is shown in FIGS. 15-17. Here the activator unit 130 is arranged in two parts. One part 160 comprises the generally tubular body 162 with proximally directed tongues 164. However, the transversal end wall 166 is not an integral part. Instead it is arranged as a separate disk-shaped part 168 that can be snap-fitted into the body 162 between stop ledges 170 and an annular inwardly directed rim 172 on the inner surface of the body 162. The proximally directed surface of the transversal end wall 166, when fitted in the body, comprises posts 174 as described above, arranged with proximally directed contact surfaces 176. However, these posts 174 have been provided with adjuster elements 178 that in the embodiment are extending pieces that are integral with the posts 174, wherein the posts 174 have been made longer in the proximal direction. In FIGS. 15-16 the posts extend generally the same amount as the previously described tubular adjuster element. Further, as seen in FIG. 17 the adjuster elements have been chosen longer than in FIGS. 15-16, wherein the extending pieces of the adjuster elements 178 make the posts extend further for handling of even shorter medicament cartridges.

It is to be understood that the embodiment described above and shown in the drawings is to be regarded as a non-limiting example of the present disclosure and that it may be modified in many ways within the scope of the patent claims.

The invention claimed is:

1. A medicament delivery device comprising:
a housing, arranged to accommodate a medicament container provided with a movable stopper;
a power unit arranged inside said housing, said power unit comprising a plunger rod, a drive spring operably arranged to act on the plunger rod and, which is, upon activation, operably arranged to act on said medicament container, an actuator comprising holding elements, capable of releasably holding said plunger rod with said drive spring in a tensioned state, and an actuator sleeve operably connected to said actuator for releasably locking said holding elements in a holding state; said medicament delivery device further comprising:
a medicament delivery member guard slidably movable in said housing and arranged to act on said actuator sleeve for setting said holding elements with said actuator sleeve in a first activation state;
an activator unit arranged to be manually operated and which is operably connected to said plunger rod for setting said holding elements with said actuator sleeve in a second activation state, wherein said activator unit comprises a number of proximally extending posts that are arranged with proximally directed surfaces,
wherein said plunger rod is released when both activation states are set,
wherein an adjuster element in contact with the proximally extending posts is operably arranged between said plunger rod and said activator unit, which adjuster element has a length dependent on the initial position of the stopper in relation to the initial position of a proximal end of the plunger rod.

2. The medicament delivery device according to claim 1, wherein said adjuster element is chosen dependent on the initial position of the stopper in relation to a support surface for said medicament container.

3. The medicament delivery device according to claim 2, wherein said support surface for said medicament container is arranged on a medicament container holder.

4. The medicament delivery device according to claim 1, wherein said drive spring is arranged inside said plunger rod; wherein said adjuster element comprises a generally tubular member and wherein said drive spring extends through said adjuster element.

5. The medicament delivery device according to claim 4, wherein said adjuster element comprises stabilizing elements arranged to prevent misalignment due to lateral forces from said drive spring.

6. The medicament delivery device according to claim 5, wherein said actuator comprises parallel side surfaces arranged to interact with said stabilizing elements of said adjuster element.

7. The medicament delivery device according to claim 1, wherein said adjuster element comprises a section of said posts directed in the proximal direction.

8. The medicament delivery device according to claim 1, wherein said holding elements comprise a number of tongues arranged with ledges arranged to engage recesses in said plunger rod.

9. The medicament delivery device according to claim 8, wherein said actuator sleeve is arranged slidable in relation to said actuator, wherein movement of said medicament delivery member guard in a distal direction causes said actuator sleeve to move distally to said first activation state.

10. The medicament delivery device according to claim 1, wherein said activator unit comprises locking elements arranged to cooperate with corresponding locking elements of said actuator for preventing movement of said activator unit in a distal direction.

11. The medicament delivery device according to claim 1, wherein the power unit further comprises a guide rod extending inside said drive spring, that said guide rod is arranged with ledges at its distal end, which ledges are connected to said actuator.

12. The medicament delivery device according to claim 11, wherein said drive spring is arranged between said ledges and a proximal wall of said plunger rod.

13. A power unit for medicament delivery device comprising:
a housing;
a plunger rod,
a drive spring operably arranged to act on the plunger rod;

an actuator comprising holding elements that releasably hold the plunger rod with the drive spring in a tensioned state, and an actuator sleeve operably connected to the actuator for releasably locking the holding elements in a holding state;

a medicament delivery member guard slidably movable in the housing and arranged to act on the actuator sleeve for setting the holding elements with the actuator sleeve in a first activation state;

an activator unit arranged to be manually operated and which is operably connected to the plunger rod for setting the holding elements with the actuator sleeve in a second activation state, wherein said activator unit comprises a number of proximally extending posts that are arranged with proximally directed surfaces; and an adjuster element in contact with the proximally extending posts and operably arranged between the plunger rod and the activator unit, where the adjuster element abuts a distal end of the plunger rod and has a length predetermined based on a known size and volume of a medicament container to be used in the medicament delivery device such that an initial position of a proximal end of the plunger rod abuts a distal end of a movable stopper inside the medicament container.

14. The power unit of claim 13, wherein the drive spring is arranged inside a hollow portion of the plunger rod.

15. The power unit of claim 13, wherein the drive spring extends through a through hole in the adjuster element.

16. The power unit of claim 13, wherein the adjuster element further comprises a generally tubular member having an outside surface.

17. The power unit of claim 15, wherein the outer surface comprises stabilizing elements that operatively engage with guide parallel side surfaces on the actuator sleeve.

18. The power unit of claim 13, wherein the power unit further comprises a guide rod positioned inside said drive spring.

* * * * *